United States Patent [19]

Corazzelli, Jr.

[11] 4,360,008
[45] Nov. 23, 1982

[54] LARYNGOSCOPE

[76] Inventor: Frank G. Corazzelli, Jr., 60 Canterbury La., Trumbull, Conn. 06611

[21] Appl. No.: 183,263

[22] Filed: Sep. 2, 1980

[51] Int. Cl.³ .............................................. A61B 1/06
[52] U.S. Cl. ........................................ 128/11; 128/18
[58] Field of Search ..................... 128/4, 11, 6, 17, 18, 128/19, 10, 200.26

[56] References Cited

U.S. PATENT DOCUMENTS

| | | | |
|---|---|---|---|
| 902,993 | 11/1908 | McIntosh | 128/17 |
| 1,945,380 | 1/1934 | Russell | 128/11 |
| 2,070,820 | 2/1937 | Allyn | |
| 2,289,226 | 7/1942 | Von Foregger | |
| 2,354,471 | 7/1944 | MacIntosh | |
| 2,433,705 | 12/1947 | Palmeter | |
| 2,630,114 | 3/1953 | Hart | 128/11 |
| 2,648,329 | 8/1953 | Mörch | |
| 3,426,749 | 2/1969 | Jephcott | |
| 3,595,222 | 7/1971 | Vellacott et al. | |
| 3,856,001 | 12/1974 | Phillips | |
| 4,085,756 | 4/1978 | Weaver | 128/17 |
| 4,086,919 | 5/1978 | Bullard | |
| 4,114,609 | 9/1977 | Moses | |
| 4,126,127 | 11/1978 | May | 128/11 |
| 4,178,920 | 12/1979 | Cawood, Jr. et al. | 128/4 |
| 4,273,112 | 6/1981 | Heine et al. | 128/11 |

Primary Examiner—Robert Peshock
Assistant Examiner—Michael J. Foycik, Jr.
Attorney, Agent, or Firm—Cifelli, Frederick & Tully

[57] ABSTRACT

The blade of a laryngoscope is elongated, extends from the handle and has disposed at its distal end a separate tip that is hingedly connected thereto and arranged to be selectively manually operated from the handle to be pivoted in a controlled and desired manner relative to the distal end of the blade to function as a depressor.

10 Claims, 11 Drawing Figures

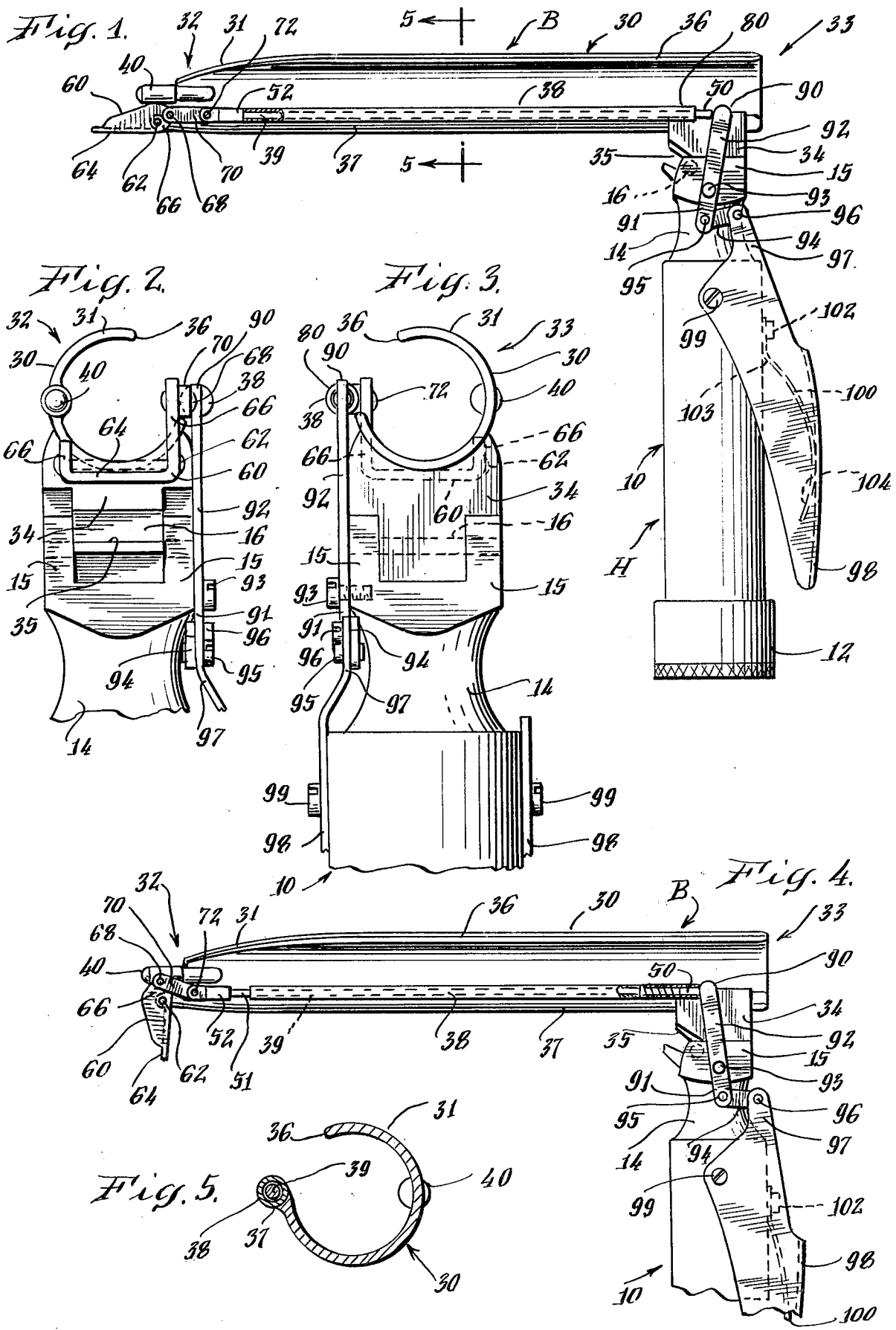

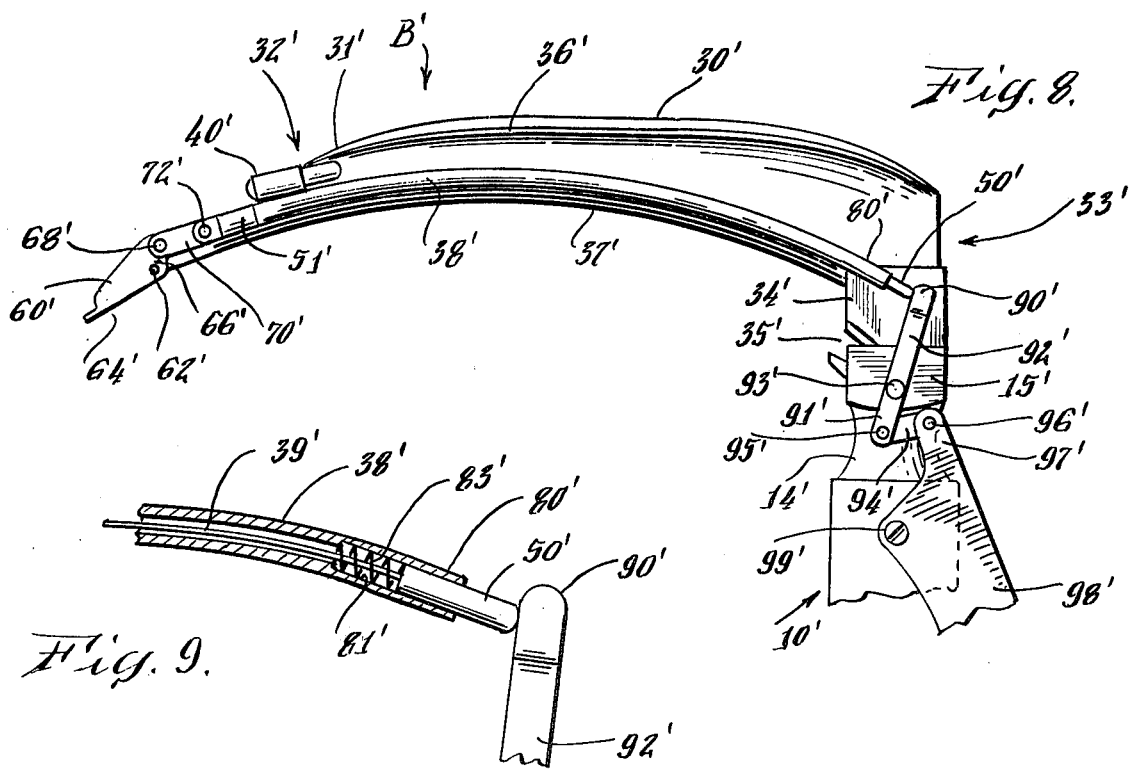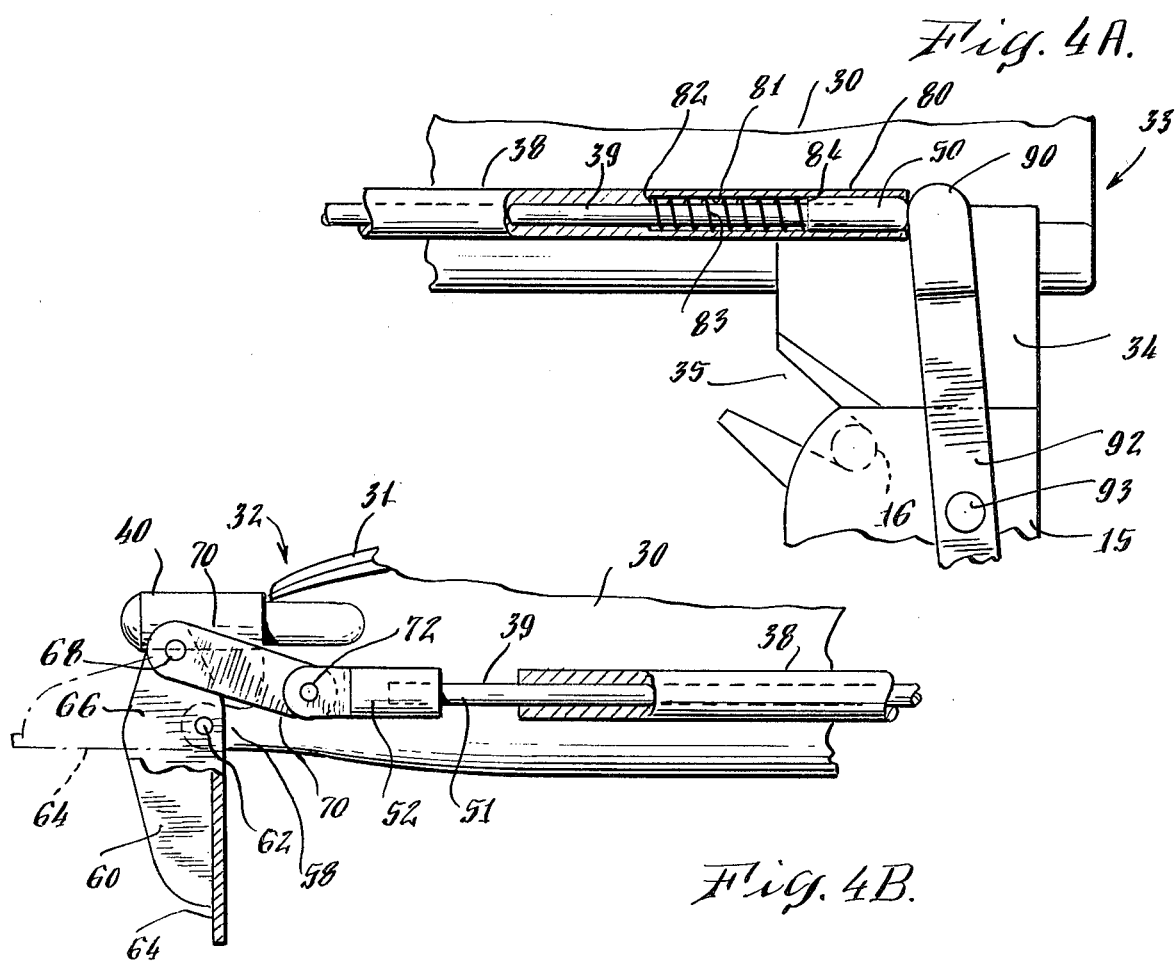

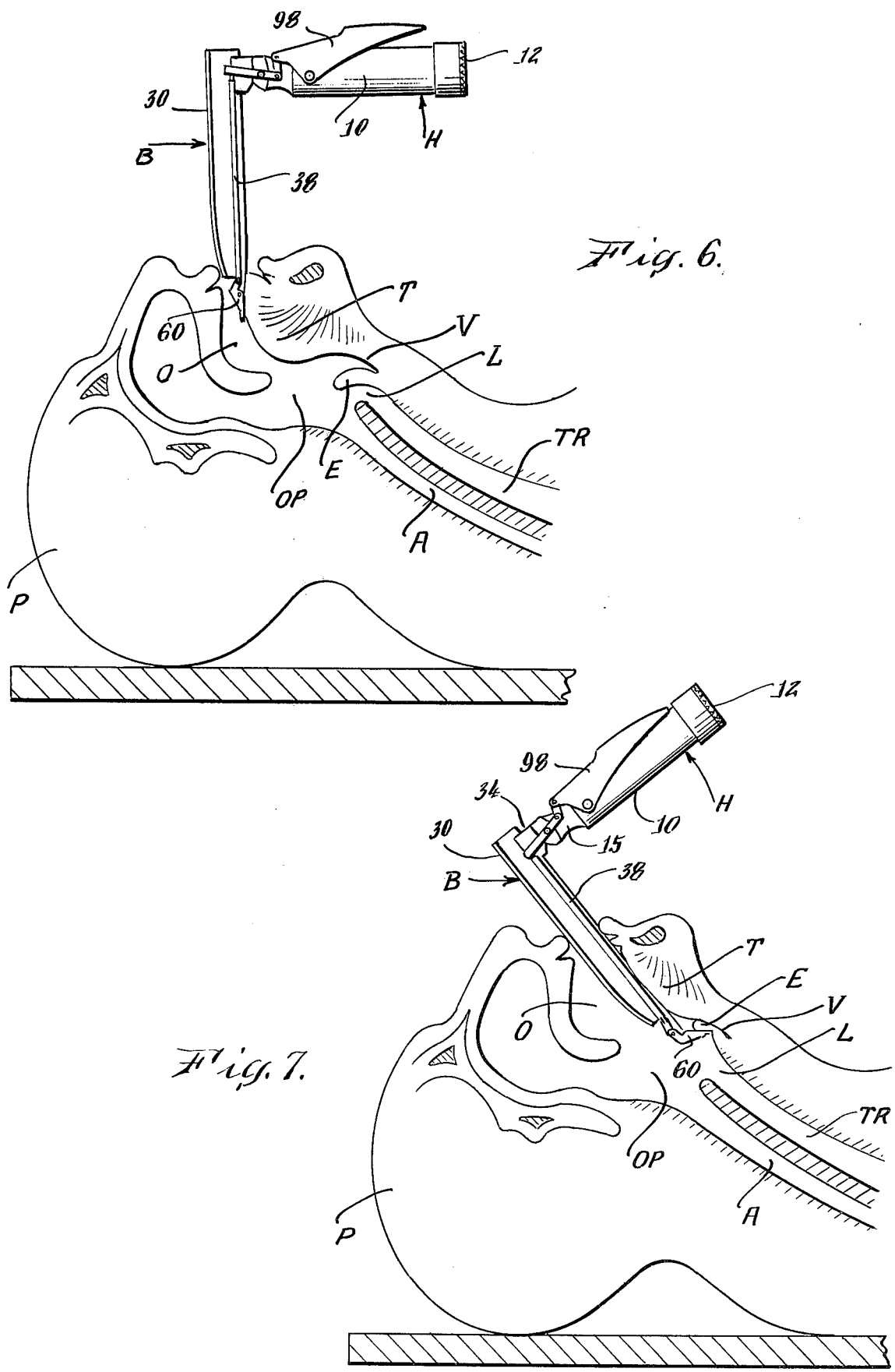

LARYNGOSCOPE

This invention relates to an improved laryngoscope, primarily for use in performing endotracheal intubation and, more particularly, to an improvement in the laryngoscope blade which enables it to be manually selectively operated to function as a highly improved depressor.

BACKGROUND OF THE INVENTION

Contemporary practice of medicine, especially in the areas of anesthesiology, critical care, intensive care and emergency room care, frequently requires the physician to pass a tube into the trachea of a patient, a procedure called endotracheal intubation, in order to provide a patent airway and prevent foreign material from entering the trachea and passing to the lungs, which might cause infection or varying degrees of collapse of the lungs. In order to intubate the trachea, it is necessary to expose the larynx. This ordinarily requires the displacement of the throat formations, primarily the epiglottis, which normally covers the larynx during the swallowing of food and water, and the passage of an appropriate tube past the vocal cords and into the trachea.

Endotracheal intubation normally is accomplished with an instrument called a laryngoscope which consists of two main portions, a handle and an elongated blade. Though some are formed of an integral piece, most current laryngoscopes have a handle and a blade formed in two separate, detachably connected parts. The handle usually is hollow and holds dry cell batteries necessary to power an illuminating lamp that is supported by the blade and employed to illuminate the throat cavity. A hinged joint is usually formed by and between the handle and the blade to permit their detachable connection. Presently available blades come in different sizes of two general types: the straight blade and the curved blade, and various modifications of each type of blade are also available. The various shapes, sizes and styles afford the physician with a variety of instruments to be used for different patient throat structures and conditions. All of the known available blades have one characteristic in common, viz., the tip of the blade is a part of, hence immovably fixed to, the body of the blade at a fixed angle. This constitutes one of the major disadvantages of known blades, which I have eliminated by my invention.

PROBLEM

The endotracheal intubation of many patients is difficult or impossible with presently available laryngoscope blades, either because of distorted anatomy, pathologic conditions, or deviations of the oral cavity from normal. Some of the conditions encountered which make intubation difficult are: protruding or carious upper incisor teeth; a narrow oral cavity; a short rigid epiglottis; a short "bull" neck, or a larynx that is more anterior than normal. With presently available blades, many times it is not possible or extremely difficult to expose the larynx due to the fixed angle of the blade tip. Patients have been known to be injured by the manipulation of known laryngoscopes by physicians, in some cases by having their teeth accidentally broken.

PRIOR ART

Those familiar with anesthesia equipment are aware of the development of the laryngoscope art and many patents have been issued on improvements in it. Perhaps one of the earliest largngoscopes developed for endotracheal intubation for anesthesia was the Jackson laryngoscope, which comprised a substantially straight blade having a tube-shaped shaft and a straight tip. The Eversol laryngoscope comprised the Jackson blade with batteries for an illuminating lamp mounted in the handle. Miller provided a laryngoscope having a blade with a small curved tip and a flange for controlling the tongue. Other straight blades are disclosed in Foregger U.S. Pat. No. 2,289,226, and Allyn U.S. Pat. No. 2,070,820. A blade curved throughout its length was developed by MacIntosh, U.S. Pat. No. 2,354,471. The Philips laryngoscope, U.S. Pat. No. 3,856,001, includes a major portion of a blade which is straight with a small portion of its tip curved and tapered. Palmeter U.S. Pat. No. 2,433,705 discloses a two-part laryngoscope with a quickly detachable hinge joint for connecting the blade and handle. Bullard U.S. Pat. No. 4,086,919 discloses a laryngoscope which includes a blade having a major straight portion, a distal end portion bent at an acute angle and a curved distal tip portion arranged for engaging the vallecula or epiglottis, all functioning to permit lifting of the epiglottis by lifting the entire instrument upwardly relative to the patient. Bullard also includes fiber optic means for permitting indirect visualization of the glottis without disturbing the patient's normal head position.

Regardless of whether the prior art laryngoscope blades are straight, curved or combinations thereof, they are all functionally rigid structures which require manipulation of the entire laryngoscope relative to the patient after it is inserted into the throat of the patient in order to move the epiglottis out of the way to permit visualization or passage of the tube to effect intubation. Such manipulation frequently involves simultaneously pulling the laryngoscope blade along its axis rearwardly and raising it relative to the patient with wrist action. These manipulations sometimes injure or complicate injuries of patients having spinal, neck or facial injuries, and frequently the laryngoscope blade contacts and is pivoted about the edge of the upper teeth and breakage or injury of the teeth often results.

BRIEF SUMMARY OF THE INVENTION

My invention is directed to an improved laryngoscope which has at its blade's distal end a tip that is selectively manually adjustable so as to dispose the tip in any convenient angular disposition relative to the main portion of the blade within a functionally operative angular range, without requiring manipulation of the entire laryngoscope. The blade may be of either the straight or curved type and of differing styles and sizes. The tip functions as a selectively operated depressor and is pivotally connected to the major portion of the blade by a hinged joint. Selectively manually operated mechanism which controls the disposition of the tip is built into the laryngoscope and enables the user to dispose the tip at any desired angle within its range of movement, all for the purpose of facilitating endotracheal intubation, especially in difficult patients. The control for the mechanism is mounted on the laryngoscope handle, whereby the user may conveniently position the pivoted tip. With the pivotal tip according to my invention, soft tissues in the laryngal area, such as the epiglottis, may be displaced selectively by the user, and the blade may be disposed in an almost direct line with the trachea, whereby good visability of the area is afforded, and an endotracheal tube may be slid along the blade between the vocal cords in a straight line into the trachea. The structural arrangement is such that the epiglottis may be selectively depressed or displaced by the pivotal tip without movement of the entire laryngoscope, much less the manipulations required by prior art laryngoscopes.

BRIEF DESCRIPTION OF THE DRAWINGS

FIG. 1 is a side elevational view of one embodiment of my improved laryngoscope having a straight blade with the distal end tip disposed in its normal position wherein it is aligned with the major axis of the blade;

FIG. 2 is an enlarged fragmentary end elevational view of the laryngoscope looking at the distal end thereof (looking from the left in FIG. 1);

FIG. 3 is a view similar to FIG. 2, but looking at the proximal end of the laryngoscope;

FIG. 4 is a fragmentary view generally similar to FIG. 1, but showing the laryngoscope selectively actuated so as to pivot the distal end tip so as to be disposed approximately 90° counter-clockwise relative to the major axis of the blade;

FIG. 4A is an enlarged view of the right end (proximal) portions of FIG. 4, and 4B is a similar view of the left end (distal) portions;

FIG. 5 is an enlarged sectional view taken substantially on line 5—5 of FIG. 1;

FIG. 6 is a diagrammatic view showing my improved laryngoscope being inserted through the mouth into the throat of a patient in supine position;

FIG. 7 is a view similar to FIG. 6, but showing the laryngoscope after being fully inserted into operative position with its tip having been selectively pivoted so as to lift the epiglottis to expose the laryngal area;

FIG. 8 is a fragmentary side elevational view of another embodiment of the invention having a curved blade; and FIG. 9 is an enlarged longitudinal sectional view through a portion of the drive mechanism for pivoting the tip.

DETAILED DESCRIPTION OF THE INVENTION RELATIVE TO THE DRAWINGS

Referring to FIGS. 1-5, and particularly FIG. 1, my improved laryngoscope is illustrated as being of the detachably connected, two-piece type. It includes a handle H and a straight blade B that are detachably connected in a known manner, as by having a connection of the type disclosed in Palmeter U.S. Pat. No. 2,433,705 to permit easy separation and attachment of the handle and blade, so as to allow for sterilization of the blade and utilization of blades of different configurations or dimensions with the handle. The handle H is preferably of the hollow type that houses one or more dry cell batteries of the flashlight type which constitute a source of electrical energy for an illuminating lamp. The handle H is a generally cylindrical hollow casing 10 and includes a detachably connected cap 12 at its lower end which permits access to the interior of the casing for placement, removal and replacement of the dry cell batteries.

The blade B is of the straight blade type, other than for the incorporation of my invention. The blade B comprises an elongated generally C cross-sectioned body 30 (see FIG. 5). The body 30 is connected at one of its ends 33 to the upper end of the handle casing 10 (its proximal end). At its other (distal) end 32, the body 30 supports a small electric illuminating lamp 40 at one side. The lamp 40 is connected in circuit with the dry cell batteries disposed within the handle H through known and suitable circuit elements, including some disconnectable ones in the detachable joint between the blade B and handle H. The details of construction of the electrical circuit means for energizing the lamp 40 to illuminate it in operation are known and form no specific part of my invention.

As the hinge joint connection between the blade B and handle H are known, they will be described only generally herein; reference to the Palmeter U.S. patent will disclose one detailed arrangement. The upper end of the casing 10 includes a head 14 having a pair of upwardly extending, laterally spaced ears 15 which support a transversely extending fixed hinge pin 16. The blade B at its proximal end 33 has a head 34 formed to cooperate with and be complementary with the head 14 of the handle so as to be detachably connectable thereto. Blade head 34 is narrowed at its lower end so as to be insertable between the ears 15 of handle head 14. A transverse slot 35 is formed in the blade head 34 and arranged to receive the hinge pin 16 of the handle head 14, when the latter is attached to the head 34. The heads 14 and 34 are configured, e.g. the slot 35 is inclined, to facilitate connection by relative movement of handle and blade. The arrangement is such as to permit the handle and blade to be pivoted relative to each other between positions in which they are closely juxtaposed and parallel, and a position wherein they extend at an approximate right angle to each other (as illustrated). In order to maintain the handle and blade in assembled condition, a spring pressed detent is carried by the blade head 34 positioned to cooperate with the hinge pin 16 to retain it in the slot 35. Other spring pressed detents are carried by the head 34 and received in suitable recesses in the opposing inner faces of the ears 15 to retain the handle and blade in assembled position and dispose them generally at right angles to each other.

As stated with reference to FIG. 5, the cross-sectional configuration of the blade body 30 is generally C-shaped, and it has that essential cross-sectional configuration throughout most of its longitudinal extent. The body thereby forms two spaced, smooth, longitudinal, straight edges 36 and 37. Edge 36 and an adjacent portion of the body 30 form a flange portion 31 which in operation is employed to displace the tongue laterally of the mouth area during and after insertion of the blade into the mouth of a patient.

Edge 37 is enlarged so as to form a longitudinal guide tube 38 for a push rod 39. Push rod 39 is disposed within guide tube 38 for relative longitudinal movement, and its proximal end 50 normally is disposed to extend beyond the proximal end of guide tube 38, which is slightly shorter than the longitudinal length of the blade body 30 (see FIG. 1). The distal end 51 of the push rod extends beyond the distal end of the guide tube and is connected to a diametrically enlarged stop link 52, which is arranged during operation to contact the guide tube to prevent full movement of the push rod distal end into the guide tube (toward the right in FIGS. 1 and 4). The lower side 58 of the distal end 32 of the blade body 30 is formed to support a separate tip 60, which is pivotally secured thereto, as by hinge pin 62 (see FIG. 4B). The tip 60 functions as a tissue depressor or displacer, and includes a smooth tissue engaging spatula portion 64 at its free end, and a pair of spaced upstanding ear portions 66 which are pivotally connected to hinge pin 62. One of the ears 66 located at the lateral side opposite the lamp 40 (see FIG. 2) is enlarged and is pivotally connected by pivot 68 to a drive link 70 at one of latter's ends, the other end of which is pivoted by pivot 72 to the link 52. The construction and arrangement is such that the tip 60 may be selectively pivoted within an approximate 90° angular range from and between its position shown in FIG. 1, wherein it extends substantially in longitudinal alignment with the blade body 30, to one in which it extends downwardly relative thereto approximately at an angle of 90°, as shown in FIG. 4. In operation, as will become apparent subsequently, the tip 60 is selectively pivoted between the FIGS. 1 and 4 positions, and to any desired intermediate angular position, in response to longitudinal movement of the push rod 39 which, in turn, is selectively manually operated.

The proximal end 80 of guide tube 38 is disposed near the proximal end of the blade body 30 but terminates short thereof (see FIG. 4A). The guide tube has an elongated passage which supports the push rod 39 throughout most of its length for relative longitudinal movement. The passageway at the proximal end has a concentrically enlarged entrance portion 81 which forms an internal annular shoulder 82. The push rod proximal end 50 is enlarged relative to the remainder of the push rod and has a shoulder 84 formed thereon which faces the distal end of the blade. A compression spring 83 is mounted on the push rod 39 and positioned in compression between the shoulders 82 and 84, thereby normally biasing the push rod toward the proximal end of the blade (toward the right in FIGS. 1, 4 and 4A) into the FIG. 1 disposition wherein the push rod is in its rightwardmost position with its stop link in contact with the distal end of the guide tube 38, and the tip 60 is axially longitudinally aligned with the blade body 30. This is the normal unpivoted position of the tip 60 when the control therefor is unactuated.

In order to selectively pivot the tip 60 (counter-clockwise as viewed in FIG. 1) toward its fully pivoted position (shown in FIGS. 4 and 4B), an actuating force must be applied to the proximal end 50 of the push rod 39 toward the distal end (the left in FIGS. 1 and 4) to move the push rod against the bias of the spring 83 toward the distal end (to the FIGS. 4, 4A and 4B position). Movement of the push rod 39 toward the distal end compresses spring 83 and causes the tip 60 to be pivoted counter-clockwise about pivot pin 62 through the drive linkage elements 52, 70 and the enlarged ear 66 (the FIGS. 4 and 4B position). The release of the actuating force automatically results in the unstressing of spring 83, which returns the push rod to the proximal end (the right in the figures) to the FIG. 1 position causing tip 60 to pivot clockwise. Therefore, to pivot the tip 60 counter-clockwise, the push rod 39 must be moved to the left relative to the blade body 30, by an actuating force, and to permit the tip 60 to pivot clockwise to return to its normal position shown in FIG. 1, the force must be removed to allow the spring 83, which has been compressed during the leftward movement of the push rod, to unstress to return the push rod toward right and thereby pivot the tip to its FIG. 1 position.

It should be understood that the blade as described thus far as part of a two-piece laryngoscope is a self-contained unit having a pivotal tip and a selectively actuated drive mechanism for it. I have devised a manually selectively operated mechanism for applying the actuating force to the push rod and incorporated it in the handle H. Therefore, the drive mechanism for the tip 60 comprises two separable sub-mechanisms, one carried by the blade and the other carried by the handle.

The push rod 39 is selectively manually moved to the left, as viewed in FIGS. 1 and 4, to pivot the tip 60 counter-clockwise by a leftwardly directed force applied to the proximal end 50 of the push rod by the upper drive end 90 of push rod actuating lever 92, which is pivotally secured at one side of the handle head 14 on pivot 93. The lower end 91 of lever 92 is pivotally secured to one end of drive link 94 by pivot 95, the other end of which is pivoted by 96 to a drive ear 97 of actuating handle lever 98. Lever 98 is generally channel-shaped in cross section, and pivoted to opposite the sides of the handle casing 10 by pivots 99. The lower portion of handle actuating lever 98 is normally biased by leaf spring 100 away from the handle casing, so as to be biased counter-clockwise about pivots 99. Spring 100 is secured at one of its ends 103 to the handle casing 10 by securing means, such as screw 102, and has its other end 104 normally stressed so as to bias the lower portion of the handle actuating lever 98 counter-clockwise. Therefore, when in its normal condition, the handle actuating lever 98 is biased about its pivots 99 counter-clockwise as viewed and to its disposition illustrated in FIG. 1. In this condition, the linkage formed by elements 92 and 94 causes the upper driving end 90 of push rod lever 92 to be moved clockwise to a position wherein it does not exert any appreciable leftward actuating force on the proximal end 50 of the push rod 39.

To selectively cause the tip 60 to pivot, the user of my improved laryngoscope grips and squeezes the handle casing 10 and handle actuating lever 98 toward each other, which can be accomplished by the use of one hand. This causes the lever 98 to rotate in a clockwise direction about its pivots 99, resulting in rightward movement of its ear 93 and link 94, which causes push rod lever 92 to rotate counter-clockwise about its pivot 93. The latter movement causes leftward movement of the drive end 90 of lever 92, which overcomes the normal bias of spring 83 and forces the push rod 39 in a leftward direction toward the distal end. The latter causes the distal end 51 of the push rod 39 to operate through the linkage comprising stop link 52, the link 70 and the large ear 66 to rotate the tip 60 counter-clockwise about its pivot pin 62. As long as the lever 98 is held in any selected position between its normal FIG. 1 disposition and its fully squeezed FIG. 4 disposition, the tip 60 will be held in the angular disposition relative to the blade body 30 to which it has been moved by the extent of squeezing of lever 98.

Release of squeezing pressure on lever 98 permits the spring 100 to unstress, thereby moving the lever 98 counter-clockwise, resulting in the drive end 92 moving toward the right to remove the force on the push rod end 50, allowing unstressing of the spring 83, and moving the push rod 39 to the right, all resulting in the clockwise unpivoting motion of the tip 60.

It should be carefully noted that my invention which provides for the selective manual pivoting of the tip at the distal blade end may be incorporated in different types of laryngoscopes including one-piece ones. It has been illustrated in FIGS. 1-5 as being incorporated in a two-piece, straight blade laryngoscope, in which the blade and handle are separable. Therefore, the selectively operated tip drive and control means is illustrated as formed partially on the separable blade B and partially on the separable handle H. In this regard, the push rod 39 and its associated parts are carried by the blade B, whereas the push rod actuating lever 92 and its associated parts are carried by the handle H. The separable interface of tip drive and control means is at the detachable force transmitting driving connection of the push rod proximal end 50 and the drive end 90 of the push rod lever 92. It will be understood by those skilled in the art that my invention may be readily incorporated in a one-piece laryngoscope.

The operation and utilization of the FIGS. 1-5 embodiment of my improved laryngoscope will now be described. To appreciate its functional advantages, first I will describe the present techniques for endotracheal intubation with prior art instruments.

With the presently available prior art straight blade laryngoscope, the accepted practice is to pass the blade through and on the right side of the opened mouth of the patient, then move it medially, thus displacing the tongue toward and to the left side of the mouth. The blade is advanced deeper into the throat toward the larynx until the epiglottis comes into view. Then, the blade is slipped under the epiglottis, and with an upward and concomitant backward movement of the entire instrument relative to the patient, caused by flexure of the physician's wrist, the epiglottis is directly elevated, thus exposing the opening of the larynx. The endotracheal tube is then guided by the blade and passed through the larynx into the trachea.

With presently available prior art curved blade laryngoscopes, the procedure is similar except that the blade is advanced until the distal tip of the blade is in the anatomical region between the tongue and the epiglottis known as the vallecula. Then, as with the straight blade, the laryngoscope is given a concomitant upward, backward movement which results in elevation of the epiglottis and exposes the larynx.

With my improved laryngoscope, intubation is effected in a substantially easier and superior manner as follows:

As with the conventional laryngoscopes, my flexible tip equipped blade is passed on the right side of the patient's opened mouth; then moved medially to displace the tongue to the left side of the mouth; advanced toward the larynx until the epiglottis is visualized, and then slipped under it. At this point, the operation of my improved laryngoscope differs from prior art instruments. The operator merely squeezes the handle actuator lever 98 to cause pivoting of the tip 60 to the desired angle necessary to elevate the epiglottis and expose the larynx. The wrist flexure manipulation of the physician to move the entire laryngoscope relative to the patient, which can be difficult and cause problems, is eliminated. If desired, of course, the blade of my improved laryngoscope may also be used as a conventional blade in the conventional manner, simply by not squeezing the lever 98.

FIGS. 6 and 7 diagrammatically illustrate the operation of my improved laryngoscope during intubation of patient P disposed in a supine position. FIG. 6 illustrates the initial step of inserting the blade B through the open mouth of the patient, in advance of inserting it further past the teeth and through the oral and laryngal passageways O and OP. Other pertinent portions of the throat area can be seen in FIG. 6 as comprising the tongue T, epiglottis E, vallecula V, larynx area L, trachea TR and esophagus A. By reference to FIG. 7, it will be seen that the laryngoscope has been fully inserted into and manipulated relative to the patient so that it occupies a position wherein the tip 60 is juxtaposed to the epiglottis E. As illustrated, the lever 98 has been squeezed on the handle H so as to pivot the tip 60 to lift the epiglottis and expose the larynx area L. In this condition, the longitudinal extent of blade B is longitudinally aligned with the trachea TR without any obstructions, thereby affording good visability. Therefore, a tube can readily be slipped into the trachea TR to effect the desired intubation. All the foregoing is accomplished with ease and safety, for the difficult and dangerous rearward and upward composite twisting movement of the entire laryngoscope is eliminated.

My invention may be embodied in the curved blade type of laryngoscope. To illustrate that application, reference may be had to FIGS. 8 and 9, wherein similar reference numerals and characters with a prime added are employed to designate parts of the curved blade embodiment which correspond to parts of the straight blade embodiment. The principal difference between the FIGS. 8 and 9 embodiment relative to the FIGS. 1-5 embodiment is that the blade B' is curved longitudinally in arcuate fashion, in accordance with the known curved type blade. A curved blade is useful in some procedures and situations encountered in intubation of some patients. In conventional operation, its use is similar to that of the conventional straight blade, except that the blade does not directly contact and displace the epiglottis. Rather, it is advanced until its tip is in the anatomical region between the tongue and the epiglottis known as the vallecula and, then, the laryngoscope is given a concomitantly upward-backward movement of the entire laryngoscope to indirectly move the epiglottis to expose the larynx. With my improved curved blade embodiment, the laryngoscope blade is inserted through the mouth of the patient in the conventional way curved blade laryngoscopes are employed, and the flexible tip 60' is advanced to the vallecula; at this time the lever 98' is squeezed against handle casing 10', so as to cause pivoting of the tip 60' to contact the vallecula area and cause the epiglottis to be elevated and expose the larynx. Of course, my improved curved blade embodiment may be used as a conventional curved blade laryngoscope in the conventional manner if desired.

Due to the curvature of the blade body 30', in order to permit selective manual actuation of the drive mechanism to pivot the tip 60', the configuration of the push rod 39' and the push rod guide 38' are modified relative to their corresponding parts in the FIGS. 1-5 straight blade embodiment. As can be seen in FIG. 8, because of the curvature of the blade body 30', its edge 37' is arcuate and, therefore, the push rod guide 38' is arcuate. The push rod 39' is also arcuate and normally has its proximal end 50' in position to be actuated by the drive end 90' of the push rod lever 92'. The distal end 51' of push rod 39' is operatively connected to drive link 70' which is, in turn, connected to ear 66' at pivot 68' to pivot the tip 60'. Because of the curvature of the push rod tube 38', to permit its longitudinal movement, the push rod 39' is slightly flexible and has a little clearance within the push rod guide tube 38', as seen in FIG. 9. The mechanism for selectively manually pivoting the tip 60' in the curved blade embodiment of FIGS. 8 and 9 is similarly constructed and operates in substantially the same manner as that of the straight blade version of FIGS. 1-5, the only differences being those dictated by the curvature of the blade B'.

My invention possesses the advantages of affording the user of the laryngoscope a substantial amount of flexibility in operation, largely resulting from the unique pivoted tip of the blade which may be selectively pivoted over an approximate angular range of 90° in a controlled manner by the user. The particular angular disposition of the pivoted tip may be selected for any particular procedure so as to be optimum for elevating the epiglottis of the patient involved by squeezing the handle actuating lever the desired amount. The undesirable composite backward-upward movement of the entire laryngoscope effected by the manipulation of the user's wrist, which is conventionally necessary when employing prior art laryngoscopes, is eliminated with my improved laryngoscope. This makes it easier and safer to intubate patients, such as those with a narrow mouth or protruding upper inciser teeth. Further, with my improved laryngoscope, it is possible to intubate some patients in which it was not possible to expose the larynx with prior art laryngoscopes having a rigid integral blade. If suitable for a particular patient, my improved laryngoscopes may be used conventionally as with straight or curved prior art blades, depending upon the requirements of the particular patient. The pivotal tip may be selectively employed, when necessary or desirable, without the undesirable manipulations of the entire instrument previously required with prior art laryngoscopes.

As previously pointed out, my invention may be incorporated in curved or straight blade laryngoscopes, or in one-piece or separable two-piece laryngoscopes. Suitable, appropriate and desirable materials may be employed. Many known metals suitable for medical instruments, manufactured and finished without any sharp or rough protrusions to injure a patient, may be used. However, known plastic materials may be used, and some parts may be disposable. The range of applications of my invention to different types of laryngoscopes is virtually unlimited and I do not limit myself to any particular type or material. I have illustrated and explained the construction and operation of two embodiments of separable two-piece, blade-handle laryngoscopes, one embodiment of which is of the straight blade type and the other the curved blade type, for convenience of disclosure.

It should be understood from the foregoing that I have satisfied the purposes of this invention by providing improved laryngoscopes which may be readily and safely used with minimal manipulation on the part of the user and, hence, minimal opportunities for injury to the patient, and which permit the exposure and visualization of the laryngal-glottis area to expose the trachea to permit inspection, examination and intubation with a maximum facility.

While the specific details of the two embodiments of my invention have been shown and described, my invention is not confined thereto, as changes and alterations may be made without departing from the spirit and scope thereof, as defined by the following claims.

I claim:

1. A laryngoscope comprising a handle and a laryngeal blade; said laryngeal blade and said handle each having a longitudinal axis, said axes being oriented relative to each other at substantially a right angle; said blade having a distal end and a proximal end relative to said handle; said proximal end being connected to one end of said handle; said blade being configured and adapted to be inserted into a patient's oral cavity by manipulation of said handle; said distal blade end comprising a separate tip; said tip being pivotally connected to the remainder of said blade; said tip being adapted to engage and depress the epiglottis of a patient in order to permit viewing of the larynx and permit intubation; and means disposed off of the axis of said blade and accessible at said handle for selectively manually pivoting said tip.

2. A laryngoscope as defined in claim 1 wherein said means includes an actuating member mounted on said handle.

3. A laryngoscope as defined in claim 1 wherein said blade is elongated and substantially straight.

4. A laryngoscope as defined in claim 3 wherein said means includes a straight push rod mounted on said blade for longitudinal movement relative thereto and normally biased toward the proximal end of said blade; the distal end of said push rod being operatively connected to said tip by mechanism which translates longitudinal movement of said push rod into pivoting of said tip; the proximal end of said push rod being operatively associated with an actuating member so as to be selectively movable toward the distal end of said blade; and a selectively manually operated member mounted on said handle and operatively associated with said actuating member so as to selectively actuate it to move said push rod.

5. A laryngoscope as defined in claim 1 wherein said blade is curved.

6. A laryngoscope as defined in claim 5 wherein said means includes a push rod mounted on said blade for longitudinal movement relative thereto, having a curvature similar to that of said curved blade and normally biased toward the proximal end of said blade; the distal end of said push rod being operatively connected to said tip by mechanism which translates longitudinal movement of said push rod into pivoting of said tip; the proximal end of said push rod being operatively associated with an actuating member so as to be selectively movable toward the distal end of said blade; and a selectively manually operated member mounted on said handle and operatively associated with said actuating member so as to selectively actuate it to move said push rod.

7. A laryngoscope as defined in claim 1 wherein said handle and blade are detachable; a portion of said means is mounted on said blade, and another portion of said means is mounted on said handle.

8. A laryngoscope as defined in claim 7 wherein said means includes a push rod mounted on said blade for longitudinal movement relative thereto and normally biased toward the proximal end of said blade; the distal end of said push rod being operatively connected to said tip by mechanism which translates longitudinal movement of said push rod into pivoting of said tip; the proximal end of said push rod being operatively associated with an actuating member so as to be selectively movable toward the distal end of said blade; said actuating member being separate from said push rod and mounted on said handle; and a selectively manually operated member mounted on said handle and operatively associated with said actuating member so as to selectively actuate it to move said push rod.

9. A laryngoscope blade suitable for performing endotracheal intubation comprising: an elongated blade body having a longitudinal axis, distal end and proximal end; said blade body being generally C-shaped in cross-section over its major longitudinal extent and having two spaced longitudinal edges; said blade being configured and adapted to be inserted into a patient's oral cavity; means at said proximal end for attaching said blade to a laryngoscope handle at substantially a right angle relative to said blade; said distal end of said blade body pivotally supporting a tip so as to be movable within an angular range of approximately 90° relative to the longitudinal axis of said blade body; said tip being adapted to engage and depress the epiglottis of a patient in order to permit viewing of the larynx and permit intubation; a push rod mounted on said blade body in a guide tube laterally offset from the axis of said body and disposed at one of said edges for longitudinal movement relative thereto; means carried by said blade body for normally biasing said push rod toward its extreme proximal position; and means operatively connecting said distal end of said push rod to said tip and which translates longitudinal movement of said push rod into pivotal movement of said tip.

10. A laryngoscope comprising a handle and a laryngeal blade detachably secured to each other at substantially a right angle; said blade being elongated and having a longitudinal axis, a proximal end and a distal end relative to said handle; said blade being configured and adapted to be inserted into a patient's oral cavity; means detachably securing said blade at its proximal end to said handle; said blade over its major longitudinal extent being generally C-shaped in cross-section and having two spaced longitudinal edges; the distal end of said blade being separated from the remainder of said blade and pivotally connected thereto so as to form a tip arranged to be movable within an angular range of approximately 90° relative to the longitudinal axis of said blade; said tip being adapted to engage and depress the epiglottis of a patient in order to permit viewing of the larynx and permit intubation; a push rod mounted on said blade in a guide tube laterally offset from the axis of said blade and disposed at one of said edges for longitudinal movement relative thereto; means carried by said blade for normally biasing said push rod toward its extreme proximal position; the distal end of said push rod being operatively connected to said tip by linkage means which translates longitudinal movement of said push rod into pivotal movement of said tip; a manually operated control lever pivotally secured to said handle; a push rod actuating lever pivotally secured to said handle and linked to said control lever to translate selective manual pivoting of said control lever into pivoting of said actuating lever; said actuating lever having a push rod actuating end that normally projects beyond said handle when said blade and handle are separated, and which is juxtaposed to the proximal end of said push rod when said blade and said handle are connected; said control lever being biased relative to said handle to a position in which it does not actuate said actuating lever, but being selectively manually moved to a position wherein it causes said actuating lever to move said push rod toward the distal end of the blade when said handle and said blade are connected, whereby said tip is selectively manually pivoted by selective manual operation of said control lever.

* * * * *